(12) United States Patent
Zabetakis et al.

(10) Patent No.: US 9,557,296 B2
(45) Date of Patent: Jan. 31, 2017

(54) METHOD FOR THE EXTRACTION AND ELECTROCHEMICAL DETECTION OF EXPLOSIVES AND EXPLOSIVE COMPONENTS IN SOILS USING ELECTRODES, FILTER PAPER, AND ELECTROLYTE

(71) Applicants: Daniel Zabetakis, Brandywine, MD (US); Scott A. Trammell, Springfield, VA (US); Walter J. Dressick, Waldorf, MD (US); David A. Stenger, Herndon, VA (US); Jasenka Verbarg, St. Louis, MO (US)

(72) Inventors: Daniel Zabetakis, Brandywine, MD (US); Scott A. Trammell, Springfield, VA (US); Walter J. Dressick, Waldorf, MD (US); David A. Stenger, Herndon, VA (US); Jasenka Verbarg, St. Louis, MO (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 286 days.

(21) Appl. No.: 14/469,895

(22) Filed: Aug. 27, 2014

(65) Prior Publication Data

US 2016/0061775 A1 Mar. 3, 2016

(51) Int. Cl.
*G01N 27/48* (2006.01)
*G01N 33/22* (2006.01)
*B64C 39/02* (2006.01)

(52) U.S. Cl.
CPC .............. *G01N 27/48* (2013.01); *B64C 39/024* (2013.01); *G01N 33/227* (2013.01); *B64C 2201/12* (2013.01)

(58) Field of Classification Search
CPC ...... G01N 27/26; G01N 27/48; G01N 33/227; G01N 33/0057
(Continued)

(56) References Cited

U.S. PATENT DOCUMENTS

| 8,815,178 B2 | 8/2014 | Bishop et al. | |
|---|---|---|---|
| 2009/0029480 A1* | 1/2009 | Loane | G01N 21/78 436/170 |

(Continued)

OTHER PUBLICATIONS

Rahman, M. A.; Won, M.-S.; Wei, P.-H.; Shim, Y.-B. Electroanalysis 2006, 18, 993.

(Continued)

*Primary Examiner* — Bach Dinh
(74) *Attorney, Agent, or Firm* — US Naval Research Laboratory; Roy Roberts

(57) ABSTRACT

Described herein is an approach using inexpensive, disposable chemical sensor probes that can be mounted on a small unmanned aerial vehicles (UAVs) and used to analyze a site (such as one known or suspected to contain explosive residue, spilled material or contaminated soil) without the need for a person to conduct ground operations at the site. The method involves contacting a soil or a surface with a filter paper wetted with a solvent, then subjecting the filter paper to voltammetry and/or spectroscopy, thus detecting a possible variation indicative of one or more analytes, wherein the solvent is selected from the group consisting of polar aprotic or protic solvents having a boiling point of at least 100° C., room temperature ionic liquids, and deep eutectic solvents.

6 Claims, 4 Drawing Sheets

(58) Field of Classification Search
USPC .......... 204/400, 415; 205/780.5–781, 786.5, 205/787, 793
See application file for complete search history.

(56) References Cited

U.S. PATENT DOCUMENTS

2013/0292512 A1* 11/2013 Erben .................. B64C 39/024
244/1 R
2015/0126834 A1* 5/2015 Wang .................. A61B 5/6833
600/345

OTHER PUBLICATIONS

Ordeig, O.; Banks, C. E.; Del?Campo, F. J.; Muñoz, F. X.; Compton, R. G. Electroanalysis 2006, 18, 1672.
Davis, J.; Moorcroft, M. J.; Wilkins, S. J.; Compton, R. G.; Cardosi, M. F. Analyst 2000, 125, 737.
Galik, M.; O'Mahony, A. M.; Wang, J. Electroanalysis 2011, 23, 1193.
Ko, W.; Jung, N.; Lee, M.; Yun, M.; Jeon, S. ACS Nano 2013, 7, 6685.
Wang, B.; Haick, H. ACS Applied Materials & Interfaces 2013, 5, 2289.
Bora, M.; Schut, D.; Baldo, M. A. Analytical Chemistry 2007, 79, 3298.
Xu, H.; Cao, K. D.; Ding, H. B.; Zhong, Q. F.; Gu, H. C.; Xie, Z. Y.; Zhao, Y. J.;Gu, Z. Z. ACS Applied Materials & Interfaces 2012, 4, 6752.
Bonifacio, L. D.; Puzzo, D. P.; Breslav, S.; Willey, B. M.; McGeer, A.; Ozin, G. A. Adv Mater 2010, 22, 1351.
Suslick, K. S.; Rakow, N. A.; Sen, A. Tetrahedron 2004, 60, 11133.

\* cited by examiner

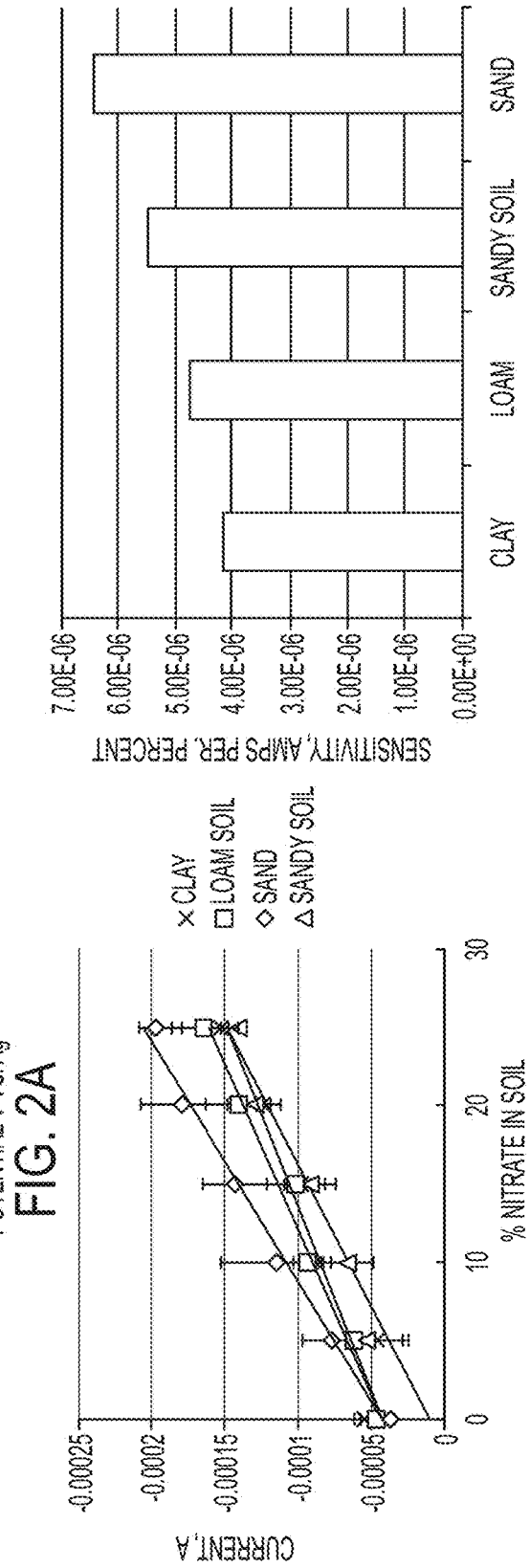
FIG. 2D
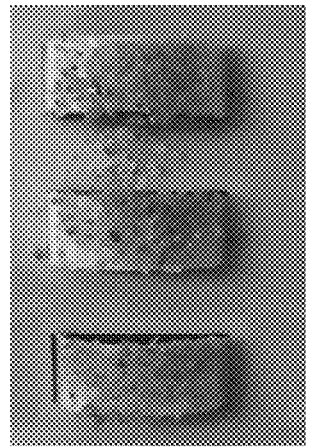
FIG. 2B
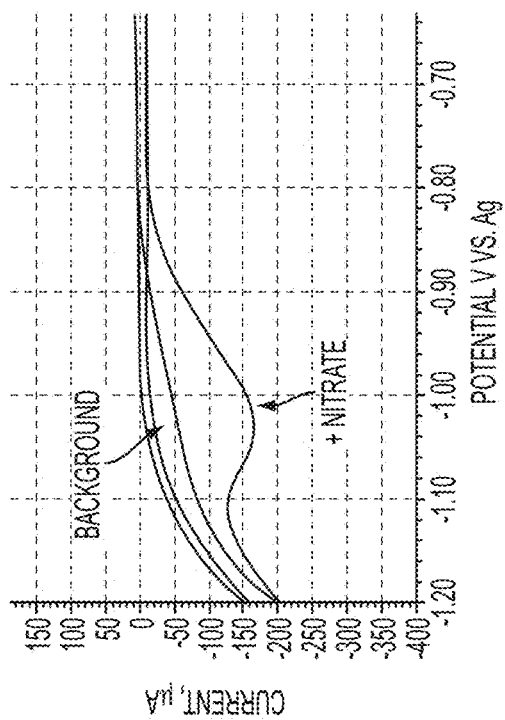
FIG. 2A
FIG. 2C

METHOD FOR THE EXTRACTION AND ELECTROCHEMICAL DETECTION OF EXPLOSIVES AND EXPLOSIVE COMPONENTS IN SOILS USING ELECTRODES, FILTER PAPER, AND ELECTROLYTE

BACKGROUND

During counterinsurgency operations, improvised explosive devices (IEDs) pose a great threat to conventional ground forces. IEDs have been based on a wide variety of explosive materials, including military explosives and propellants, agricultural materials (e.g. ammonium nitrate), industrial explosives, and a non-standard exotic chemical explosives (e.g. potassium chlorate or organic peroxides). Counterinsurgency strategy involves the determination of materials transfer points and IED manufacturing locations. Thus, there is a strong demand for explosives detection and identification. A simple, rapid and reliable method in the field would be a significant enabler of military operations.

Current technology deployed in the field for detection and identification of explosives has a number of limitations. Deployable lab systems using liquid chromatography and mass spectrometry for chemical identification are not acceptable for time-sensitive missions and require logistic support. In addition, hand held systems for chemical identification including IR spectroscopy (TruDefender) and Raman spectroscopy (FirstDefender) need bulk samples that are frequently not available. Other developing technologies include detection of volatile organic compounds (VOCs), often referred to as electronic nose or tongue technology. These comprise colorimetric and fluorescent arrays (see refs. 1-3), modified field effect transistors (see refs. 4,5), and modified quartz resonators (see ref. 6). The use of fluorescent semiconductor polymers for explosives detectors may detect common military-grade compounds used in homemade explosives and IEDs, including pentaerythritol tetranitrate (PETN). However, all these instruments require manual collection or analysis by persons directly at the suspect sites.

Remote sensing technology capable of detecting explosives at an appreciable distance, although highly desirable, has not been perfected despite considerable research. For example laser systems for standoff detection including hyperspectral imaging are of low sensitivity in soils, in that the target may be less than one pixel and signature may not be distinguishable from background.

A need exists for a simple and inexpensive method for detecting explosives, particularly using remote sensing.

BRIEF SUMMARY

A first embodiment is a method of detection involving contacting a soil or a surface with a filter paper wetted with a solvent, then subjecting the filter paper to voltammetry (e.g., cyclic voltammetry), thus detecting a possible variation in current indicative of one or more analytes, wherein the solvent is selected from the group consisting of room temperature ionic liquids, deep eutectic solvents, and polar aprotic or protic solvents having a boiling point of at least 100° C.

In a second embodiment, spectroscopy is used in place of or in addition to voltammetry.

In another embodiment, a testing rig for performing the first and/or second embodiment is operably connected to an unmanned aerial vehicle (UAV). The detection may be completed on board the UAV (with results communicated, e.g., via radio), or the UAV may capture a sample on filter paper in one location for analysis at a second location.

BRIEF DESCRIPTION OF THE DRAWINGS

In FIG. 1A, pre-soaked filter paper with the extraction solvent/electrolyte is used for retrieval, while FIG. 1B illustrates "in situ" soil analysis. FIG. 1C illustrating an optional paper chromatography step is shown in which the extraction solvent/electrolyte is "wicked" onto dry filter paper to remove interferrents and move the analyte to the electrode for detection.

FIG. 2A illustrates cyclic voltammograms of a mixture of ethylene glycol and choline chloride (background) plus 13 mM potassium nitrate recorded at a Cu modified glassy carbon electrode. FIG. 2B shows filter paper strips saturated with the mixture of ethylene glycol and choline chloride mounted on the flexible sampler having been pressed into soil containing nitrates. FIG. 2C shows current measured at −1 V vs Ag/AgCl reference electrode from cyclic voltammograms of paper strips placed on screen printed electrodes containing a Cu film. The paper strips were mounted on the flexible sampler and pressed into different soil types containing various percentages of potassium nitrate. FIG. 2D illustrates the sensitivity of detection of nitrates for the system in different soil types.

FIG. 3A shows the experimental setup. FIG. 3B shows TNT detection in sand. FIG. 3C shows the electrochemical response of natural organic matter extracted from soil samples for West Africa without paper filtration and with paper filtration. FIG. 3D illustrates an example of a typical humic acid having a variety of components including quinone and phenol, and catechol molecules that are electrochemically active and should be removed for trace explosives detection.

DETAILED DESCRIPTION

Definitions

Figure 1A:
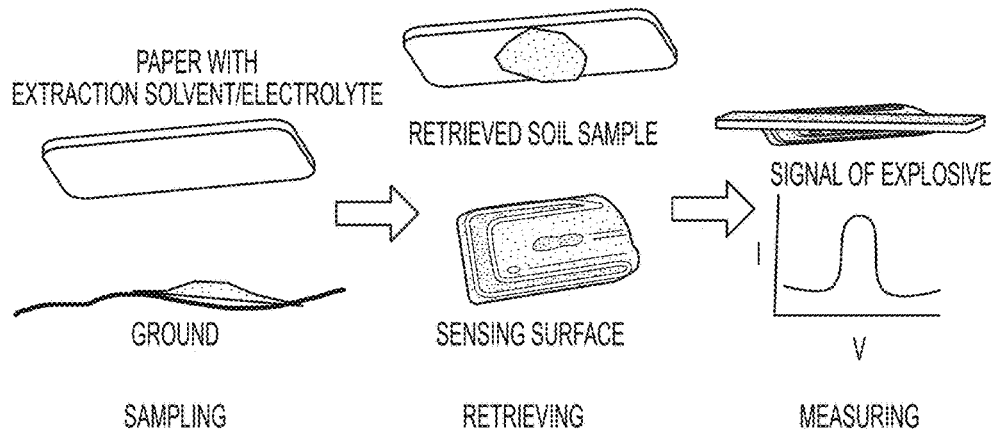
FIGS. 1A through 1C show exemplary methods of detection.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Described herein is an approach using inexpensive, disposable chemical sensor probes that can be mounted on a small unmanned aerial vehicles (UAVs) and used to analyze a site (such as one known or suspected to contain spilled material or contaminated soil) without the need for a person to conduct ground operations at the site. Possible applications include the enabling of autonomous systems to carry out the remote electrochemical detection of chemicals of importance to military missions, particularly detecting explosives. While explosives detection is the main intent of this technology, this sampling system would also be useful for detection of other chemicals, such as illicit drugs, nerve agents, other chemicals of interest such as toxic industrial compounds (TICs), biologicals, and other electrochemically active analytes of interest.

It is possible to integrate sample collection, processing and analysis of samples taken from complex soil and on surfaces with contaminating interferrents. A combination of electrodes (optionally modified electrodes) with filter paper (preferably a paper based on cellulose) absorptive coupon infiltrated with a suitable solvent can used for the extraction and electrochemical detection of explosives and explosive components in soils, as well as other possible analytes. The electrodes are typically metal or carbon and may be discrete parts in physical contact with the filter paper or optionally in the form of metal or carbon impregnated into the filter paper fibers.

In the case of a preferred solvent mixture of ethylene glycol and choline chloride, also known as ethanal, the ethylene glycol can extract nitro-aromatic, nitrates or other explosives from soils, and the choline chloride provides for the electrolyte for the detection of analytes via electrochemistry using modified electrodes.

Suitable Solvents and Analysis

In a preferred embodiment, the solvent is a deep eutectic solvent, for example a deep eutectic mixture of ethylene glycol and choline chloride such as can be obtained from a 2:1 mol ratio of ethylene glycol and choline chloride. Other suitable solvents include room temperature ionic liquids (RTILs, which are salts that are liquid at room temperature, not to be confused with salts dissolved in another liquid), and high boiling (thus having a low evaporation rate) polar aprotic or protic solvents such as dimethyl sulfoxide (DMSO) or dimethylformamide (DMF). A low rate of evaporation is desirable as it allows time for the analysis to be performed without requiring a sealed chamber or the like to reduce evaporation.

Preferably, the solvents are able to dissolve and extract nitro-aromatic, nitrates, and/or other explosives from soils across abroad temperature range without significant evaporation, and in combination with dry filter paper permits capillary movement of the solubilized analytes to allow for the detection of the analytes via electrochemistry.

In on embodiment, the solvent has a boiling point of 100° C. or greater, measured at a pressure of one atmosphere. Further embodiments may feature solvents boiling at about, e.g., 110° C. or greater, 120° C. or greater, 130° C. or greater, 140° C. or greater, or 150° C. or greater. For example, DMF boils at 153° C. while DMSO boils at 189° C.

Figure 1B:
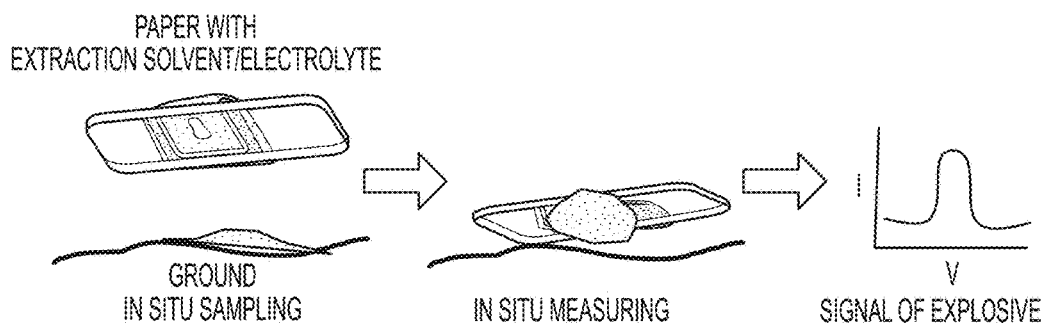
Figure 1C:
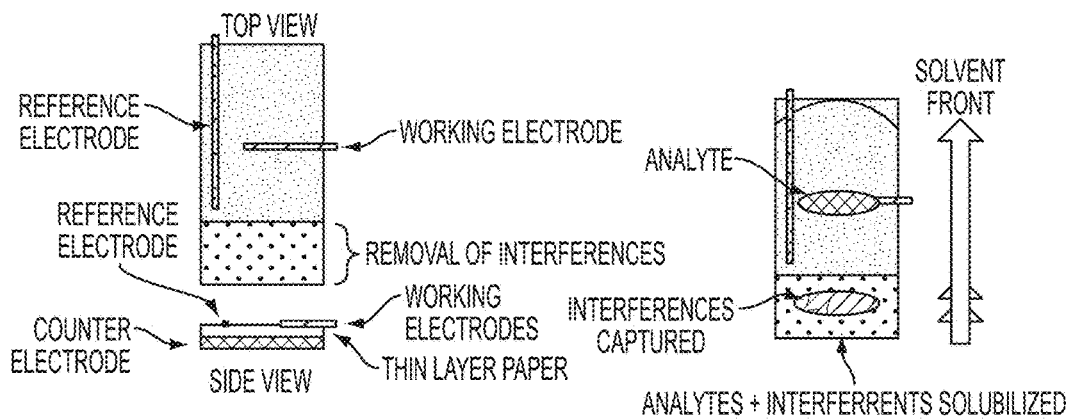

FIGS. 1A through 1C show exemplary methods of analysis. In the first two examples, pre-soaked filter paper with the extraction solvent/electrolyte is used to directly sample the soil with no extra processing step before the analyses. The measurement can either be retrieved by an unmanned aerial vehicle (UAV) for rapid analysis and further testing (FIG. 1A) or be made "in situ" (FIG. 1B) in conjunction with a UVA instrument system and radio back position and results. In the third example (FIG. 1C), a paper chromatography step is added by a wicking action in which the extraction solvent/electrolyte added to the dry paper removes interferrents and moves the analyte to the electrode for detection.

In a preferred embodiment, the paper is analyzed by electrochemical analysis, such as voltammetry including cyclic, square wave, and/or linear sweep voltammetry. Voltammetry can be conducting using one or more types of electrodes. Optionally such electrodes may be modified, for example by electroplating to obtain, e.g., a copper-modified carbon electrode. The electrodes may optionally be cleaned, polished, and/or electrochemically activated, and/or otherwise treated as known in the art. Exemplary electrodes include glassy carbon electrodes and/or screen printed electrode as well as other types known the in art such as electrodes of graphite, graphene, and/or graphene oxides. An analyte of interest may be detected by a variation in the current measured the working electrode and the counter electrode at a specific potential measured relative to a reference electrode as compared to either an expected current (for example, one stored in memory of a device), or current measured in a control sample.

Common military-grade explosives give distinctive electrochemical signatures at carbon electrodes, while Cu and Mo/W modified electrodes can detect nitrates (as in ref. 8) and chlorates (as in ref. 9). Techniques for electroanalysis described in refs. 7-10 and variants thereof may be employed, as apparent to one skilled in the art. Variations in electrochemical signature (e.g., current in analysis by voltammetry) can indicate the a degree of presence (or lack thereof) of one or more analytes. In embodiments, the variations may be detected automatically.

It is also possible to use the filter paper to obtain samples for spectroscopic analysis, as it is believed this use of the paper would remove interferrents and possible increase detection limits. Exemplary forms of spectroscopic analysis include the use of a Fourier transform infrared (FTIR) spectrophotometer (e.g., the TruDefender™), Raman spectroscopy (used by the FirstDefender™), and other related techniques such as those involving a polymer which changes optical properties on contact with an analyte.

FIGS. 2A-2D show exemplary reduction to practice for the electrochemical detection of nitrates in different soils types. In this case, the electrochemical detection of nitrates is accomplished by a carbon electrode modified with a Cu film. The electrochemical response of nitrate in a mixture of ethylene glycol and choline chloride is shown in FIG. 2A. There is a clear signal for nitrate detection above the background with a cathodic peak potential at −1.02 V vs. Ag/AgCl as measured in the cyclic voltammograms. Furthermore, the solvent is air saturated, demonstrating that reduction of oxygen does not interfere with the measurement. This is an important advantage, as oxygen reduction can obscure voltammetric peaks associated with the presence of an analyte, complicating its determination and detection.

To analyze sample soils containing nitrates at various percentages, filter paper saturated with solvent/electrolyte is mounted on a flexible holder. The paper is then pressed on to the surface of the soil manually or by a robot. The flexible holder conforms to the shape of the surface, evenly sampling the soil onto the filter paper as shown in FIG. 2B. The filter paper has several characteristics and serves multiple functions; it embodies the solvent/electrolyte for extraction and electrochemical detection and is light weight and disposable. As shown in FIG. 1C, the mixture of ethylene glycol and choline chloride on the filter paper is able to solubilize and extract the nitrates from the four different basic soil types. The signal was recorded at −1.0 V vs. Ag/AgCl from cyclic voltammograms measured on copper-modified screen printed electrodes on which the filter paper was placed on top soiled side down.

One surprising and unexpected aspect emerged from this testing: the soil did not foul the copper-modified screen printed electrodes. The sensitivity of the response for the detection of nitrates varied with the different soil types in which sand gives the largest response and clay the smallest.

Figure 3A:
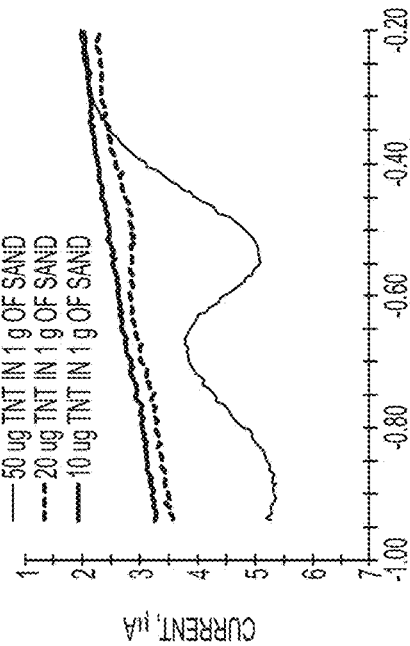
FIGS. 3A through 3D relate to the detection of trinitrotoluene (TNT) in sand using ethylene glycol and choline chloride as the extraction solvent, mobile phase and electrolyte.
Figure 3B:
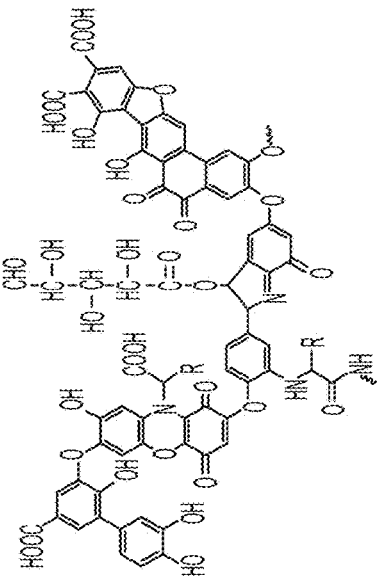
Figure 3C:
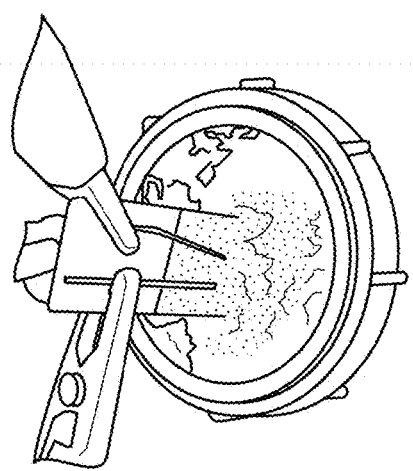
Figure 3D:
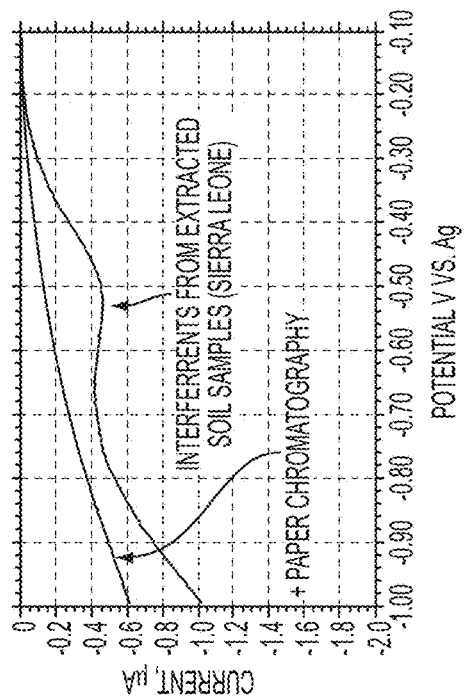

Another example is illustrated in FIGS. 3A-3D, showing the electrochemical detection of TNT in sand with using ethylene glycol/choline chloride as the extraction solvent, mobile phase and electrolyte. In this case, ethylene glycol/choline chloride is able to extract TNT from the sand and then is wicked by the filter paper onto the carbon electrode (FIGS. 3A and B). This process is able to detect TNT in sand at 20 ppm level. Moreover, the process of wicking through the filter paper can also remove interfering electrochemical signals. Using soil samples from West Africa, FIG. 3C shows the electrochemical response of an interferrent which is most likely extracted natural organic matter (FIG. 3D) which can be removed by the paper chromatography step. Thus, the filter paper can facilitate paper chromatography wherein one or more analytes move across the filter paper prior to said subjecting it to cyclic voltammetry or spectroscopy.

Unmanned Aerial Vehicle

This method is amenable to being carried out through the use of an unmanned aerial vehicle (UAV). Suitable UAVs may be directed in real time by an operator and/or operate autonomously. They may optionally include one or more still and/or video cameras and may take the form of a rotorcraft having one or more rotors, a fixed wing aircraft, or other forms of aerial vehicle.

Figure 4:
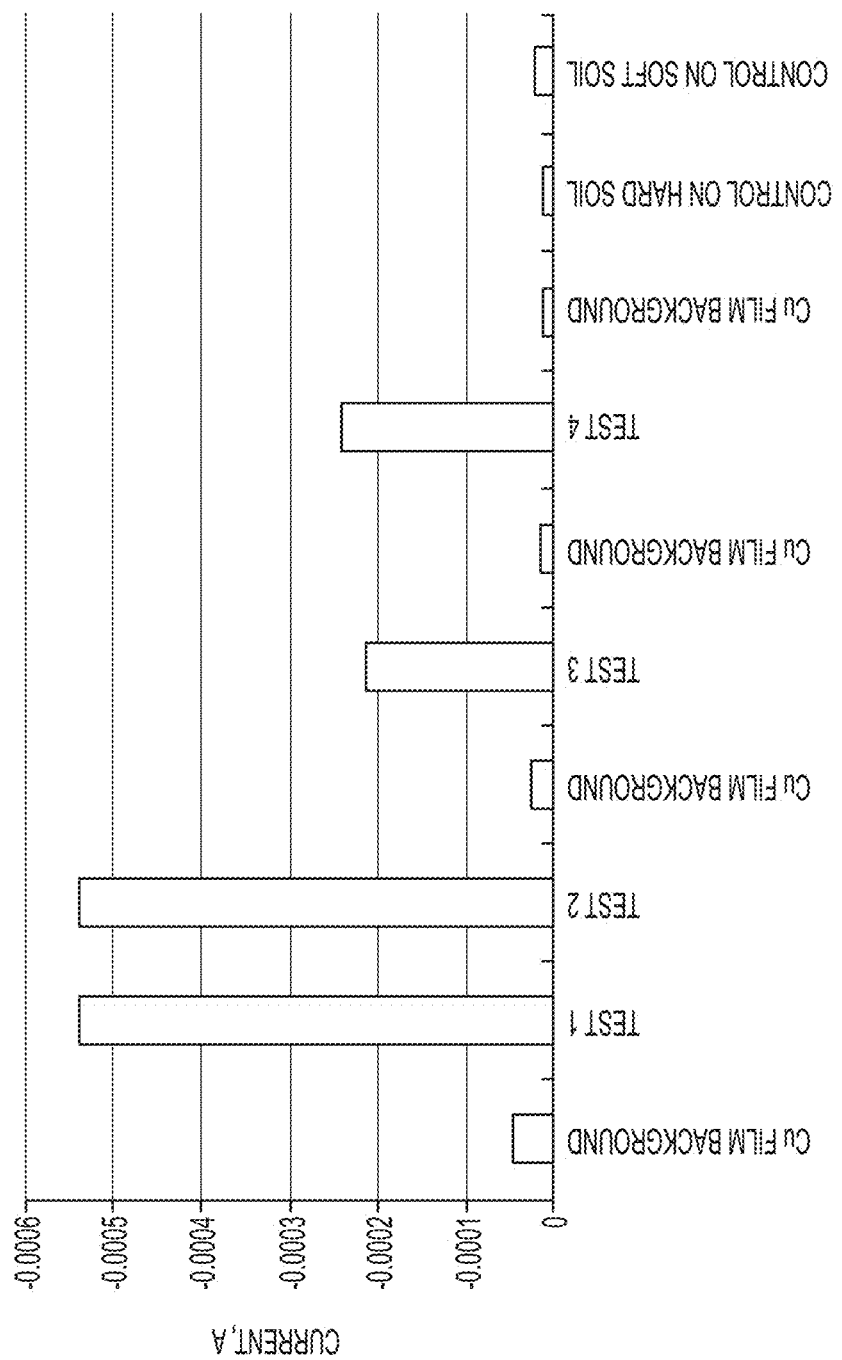
FIG. 4 shows the signal for the reduction of nitrate measured at −1 V vs Ag/AgCl from cyclic voltammograms of paper strips placed on screen printed electrodes containing a Cu film.

Experiments demonstrated use of a UAV to remotely sample soil for electrochemical detection. A sampler was amounted on an UAV and was used to sample spilled nitrates in soil at a remote target. The samples were retrieved and rapidly analyzed at a copper-modified screen printed electrode. The detection of nitrate was clearly demonstrated as shown in FIG. 4, in which the signal is well above the background levels measured in control samples. This demonstrates that the filter paper with soil and high boiling solvent is stable enough to transport back for later analysis.

In embodiments, solvent is applied after filter paper contacts a surface to be analyzed. This may include injection of a solvent aliquot into a contacted and/or collected sample to solubilize/extract one or more analytes of interest, followed by contact of the filter paper to the sample wetted with solvent to initiate analyte transport from the sample onto the filter paper to the electrode.

In embodiments, a test rig is attached to an unmanned aerial vehicle platform. The test rig includes filter paper, suitable solvent, and optionally a testing device. The filter paper may be pre-wetted with the solvent or the test rig could include a mechanism for wetting the filter paper (for example, a solvent reservoir and a pump). The testing device is operable to conduct analysis as described herein, either by voltammetry or spectroscopy or both.

The detection may be completed on board the UAV (with automated analysis followed by results communicated, e.g., via radio), or the UAV may capture a sample on filter paper in one location for analysis at a second location.

Advantages

Because of the viscous nature of ethylene glycol, it is a non-obvious choice for an electrochemical solvent since analytes would have a smaller diffusion coefficient attenuating the signal. However because of this property, the filter paper saturated with the ethylene glycol is able to capture and retrieve soil samples directly using a UAV.

Ethylene glycol/choline chloride is very slow to evaporate and acts as both an electrolyte with large potential window for electrochemical detection and as a solvent to extract nitro-aromatic compounds and other explosive components from soil.

Using this technique with filter paper, the electrodes do not foul in the presence of soil and are able to respond to the desired analyte. This is counter-intuitive and non-obvious since it was expected that the soils would block and foul the electrodes.

The detection of TNT or nitrate is accomplished in air saturated solvents demonstrating that the reduction of oxygen does not interfere with the measurement, eliminating the need to purge the system with argon or nitrogen (a common practice in electroanalytical bench top experiments) which would complicate field work.

For trace level detection, the wicking property of the filter paper is able to remove electrochemically active interferences which are most likely natural organic matter containing quinone and catechol chemical moieties. Impurities stick to the paper away from the electrodes, while the explosives remain soluble in the liquid and can reach the electrode for detection.

The paper surface can optionally be selected and/or modified to bind impurities having specific functional groups not the same as those of the explosives to remove those impurities from the sample before electrochemistry.

For other explosives of interest including chlorates and peroxides, the electrodes can be modified with catalysts to detect chlorates and indirect electrochemical schemes can be incorporation in the chemistry of the filter paper for the detection of peroxide.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES (1) Suslick, K. S.; Rakow, N. A.; Sen, A. *Tetrahedron* 2004, 60, 11133.
(2) Bonifacio, L. D.; Puzzo, D. P.; Breslav, S.; Willey, B. M.; McGeer, A.; Ozin, G. A. *Adv Mater* 2010, 22, 1351.
(3) Xu, H.; Cao, K. D.; Ding, H. B.; Zhong, Q. F.; Gu, H. C.; Xie, Z. Y.; Zhao, Y. J.; Gu, Z. Z. *ACS applied materials & interfaces* 2012, 4, 6752.
(4) Bora, M.; Schut, D.; Baldo, M. A. *Analytical Chemistry* 2007, 79, 3298.
(5) Wang, B.; Haick, H. *ACS applied materials & interfaces* 2013, 5, 2289.

(6) Ko, W; Jung, N.; Lee, M.; Yun, M.; Jeon, S. *Acs Nano* 2013, 7, 6685.
(7) Galik, M.; O'Mahony, A. M.; Wang, J. *Electroanalysis* 2011, 23, 1193.
(8) Davis, J.; Moorcroft, M. J.; Wilkins, S. J.; Compton, R. G.; Cardosi, M. F. *Analyst* 2000, 125, 737.
(9) Ordeig, O.; Banks, C. E.; Del Campo, F. J.; Mũnoz, F. X.; Compton, R. G. *Electroanalysis* 2006, 18, 1672.
(10) Rahman, M. A.; Won, M.-S.; Wei, P.-H.; Shim, Y.-B. *Electroanalysis* 2006, 18, 993.

What is claimed is:

1. A method of detection, comprising:
   contacting a soil or a surface with a filter paper wetted with a solvent, then
   subjecting the filter paper to voltammetry, thus detecting a possible variation in current indicative of one or more analytes,
   wherein the solvent is the deep eutectic solvent consisting of a mixture of ethylene glycol and choline chloride.
2. The method of claim 1, wherein said one or more analytes includes an explosive.
3. The method of claim 1, wherein said one or more analytes includes a drug, nerve agent, biothreat, pesticide, or industrial pollutant.
4. The method of claim 1, further comprising allowing migration of at least one of said one or more analytes across said filter paper prior to said subjecting to voltammetry.
5. The method of claim 1, wherein said voltammetry comprises cyclic voltammetry using a copper-modified screen printed electrode and/or carbon electrode.
6. The method of claim 1, wherein said contacting is performed by an unmanned aerial vehicle.

* * * * *